US008992952B2

(12) United States Patent
Vehige et al.

(10) Patent No.: US 8,992,952 B2
(45) Date of Patent: *Mar. 31, 2015

(54) COMPOSITIONS FOR DELIVERY OF THERAPEUTICS INTO THE EYES AND METHODS FOR MAKING AND USING SAME

(71) Applicant: Allergan, Inc., Irvine, CA (US)

(72) Inventors: Joseph G. Vehige, Laguna Niguel, CA (US); James N. Chang, Newport Beach, CA (US); Richard Graham, Irvine, CA (US); Robert T. Lyons, Laguna Hills, CA (US); Teresa H. Kuan, Placentia, CA (US); Chin-Ming Chang, Tustin, CA (US)

(73) Assignee: Allergan, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/933,807

(22) Filed: Jul. 2, 2013

(65) Prior Publication Data

US 2013/0296396 A1    Nov. 7, 2013

Related U.S. Application Data

(63) Continuation of application No. 10/911,966, filed on Aug. 5, 2004, now Pat. No. 8,512,717.

(60) Provisional application No. 60/493,178, filed on Aug. 7, 2003, provisional application No. 60/493,188, filed on Aug. 7, 2003.

(51) Int. Cl.
*A61K 9/00* (2006.01)
*A61K 31/00* (2006.01)
*A61K 31/407* (2006.01)

(52) U.S. Cl.
CPC .............. *A61K 9/0048* (2013.01); *A61K 31/00* (2013.01); *A61K 31/407* (2013.01)
USPC .......................................................... 424/400

(58) Field of Classification Search
USPC .......................................................... 424/400
See application file for complete search history.

(56) References Cited

U.S. PATENT DOCUMENTS

| | | |
|---|---|---|
| 3,278,447 A | 10/1966 | McNicholas |
| 3,890,319 A | 6/1975 | Danielewicz |
| 4,089,969 A | 5/1978 | Muchowski |
| 4,382,892 A | 5/1983 | Hayakawa |
| 4,407,792 A | 10/1983 | Schoenwald |
| 4,454,151 A | 6/1984 | Waterbury |
| 4,474,787 A | 10/1984 | Cairns |
| 4,861,514 A | 8/1989 | Hutchings |
| 5,017,229 A | 5/1991 | Burns |
| 5,021,416 A | 6/1991 | Gluchowski |
| 5,045,121 A | 9/1991 | Hoffman |
| 5,089,509 A | 2/1992 | Chandraratna |
| 5,106,615 A | 4/1992 | Dikstein |
| 5,110,493 A | 5/1992 | Cherng-Chyi |
| 5,212,162 A | 5/1993 | Missel |
| 5,215,991 A | 6/1993 | Burke |
| 5,281,591 A | 1/1994 | Burke |
| 5,382,591 A | 1/1995 | Barberich |
| 5,414,011 A | 5/1995 | Fu |
| 5,459,133 A | 10/1995 | Neufeld |
| 5,460,834 A | 10/1995 | Bhagat |
| 5,527,893 A | 6/1996 | Burns |
| 5,558,876 A | 9/1996 | Desai |
| 5,648,074 A | 7/1997 | Park |
| 5,688,819 A | 11/1997 | Woodward |
| 5,703,077 A | 12/1997 | Burke |
| 5,721,275 A | 2/1998 | Bazzano |
| 5,773,440 A | 6/1998 | Burke |
| 5,807,541 A | 9/1998 | Aberg |
| 5,811,446 A | 9/1998 | Thomas |
| 5,858,346 A | 1/1999 | Vehige |
| 5,888,493 A | 3/1999 | Sawaya |
| 5,922,773 A | 7/1999 | Lipton |
| 6,056,950 A | 5/2000 | Saettone |
| 6,255,299 B1 | 7/2001 | Deleuran |
| 6,627,210 B2 | 9/2003 | Olejnik |

(Continued)

FOREIGN PATENT DOCUMENTS

| | | |
|---|---|---|
| EP | 0306984 | 3/1989 |
| EP | 0390071 | 10/1990 |

(Continued)

OTHER PUBLICATIONS

Donshik et al., Efficacy and safety of ketorolac tromethamine 0.5% and levocabastine 0.05%: a multicenter comparison in patients with seasonal allergic conjunctivitis, Adv Ther. Mar.-Apr. 17, 2000(2):94-102, printed from http://www.ncbi.nlm.nih.gov/pubmed/11010060, 2 pages, abstract only.*
Rowe, Handbook of Pharmaceutical Excipients-Carboxymethylcellulose Sodium, Pharmaceutical Press, May 2003, 97-100.*
Acular LS® Prescription Information, 4 pages, Retrieval Date: Jan. 6, 2012, http://www.allergan.com/assets/pdf/acular_ls_pi.pdf.
Acular PF, 5 pages, Retrieval Date: Jan. 6, 2012, http://www.drugs.com/pro/acular-pf.html?printable=1.
Acular® Product Label, 5 pages, Retrieval Date: Jan. 6, 2012, http://www.drugs.com/pro/acular.html?printable=1.
Ahuja, Munish et al, Topical Ocular Delivery of NSAIDs, The AAPS Journal, Jun. 2008, 229-241, 10(2).

(Continued)

*Primary Examiner* — Gigi Huang
(74) *Attorney, Agent, or Firm* — Mark D. Kafka

(57) ABSTRACT

The present invention provides for compositions for administering a therapeutically effective amount of a therapeutic component. The compositions may include an ophthalmically acceptable carrier component; a therapeutically effective amount of a therapeutic component; and a retention component which may be effective to reduce wettability, induce viscosity, increase muco-adhesion, increase meniscus height on a cornea of an eye and/or increase physical apposition to a cornea of an eye of a composition.

10 Claims, 1 Drawing Sheet

(56) References Cited

U.S. PATENT DOCUMENTS

| | | | |
|---|---|---|---|
| 7,045,121 | B2 | 5/2006 | Chang |
| 7,141,607 | B1 | 11/2006 | Si |
| 7,491,383 | B2 | 2/2009 | Woodward |
| RE41,134 | E | 2/2010 | Bazzano |
| 7,842,714 | B2 * | 11/2010 | Farnes et al. .......... 514/413 |
| 8,512,717 | B2 * | 8/2013 | Vehige et al. .......... 424/400 |
| 2002/0103255 | A1 | 8/2002 | Hellberg |
| 2002/0198209 | A1 | 12/2002 | Woodward |
| 2002/0198210 | A1 | 12/2002 | Woodward |
| 2003/0069286 | A1 | 4/2003 | Chen |
| 2004/0224010 | A1 | 11/2004 | Hofland |
| 2004/0248962 | A1 | 12/2004 | Muller |
| 2005/0031697 | A1 | 2/2005 | Vehige |
| 2007/0254841 | A1 | 11/2007 | Ousler, III |
| 2007/0287741 | A1 | 12/2007 | Herzberg |
| 2007/0299124 | A1 | 12/2007 | Ousler, III |
| 2008/0039398 | A1 | 2/2008 | Ousler, III |
| 2008/0070988 | A1 | 3/2008 | Woodward |
| 2008/0275118 | A1 | 11/2008 | Shaw |
| 2009/0010850 | A1 | 1/2009 | Ousler, III |
| 2009/0270392 | A1 | 10/2009 | Old |

FOREIGN PATENT DOCUMENTS

| | | |
|---|---|---|
| EP | 0524587 | 1/1993 |
| EP | 0590786 | 4/1994 |
| EP | 0705878 | 4/1996 |
| GB | 2007091 | 5/1979 |
| WO | 92-002515 | 2/1992 |
| WO | 92-20349 | 11/1992 |
| WO | 93-17664 | 9/1993 |
| WO | 00-54762 | 9/2000 |
| WO | 01-01959 | 1/2001 |
| WO | 02-05853 | 1/2002 |
| WO | 03-051332 | 6/2003 |
| WO | 2004-112750 | 12/2004 |
| WO | 2005-101982 | 11/2005 |
| WO | 2006-071601 | 7/2006 |
| WO | 2009-111418 | 9/2009 |

OTHER PUBLICATIONS

Allergan "Refresh Lubricant Eyedrops" retrieved on Apr. 3, 2003 from: www.drugstore.com/qxp72838_333181_sespider/allergan/refresh_liquigel_lubricant_eye_drops.htm.

Aqualon® CMC, Physical and Chemical Properties, Hercules incorporated, printed from: http://www.herc.com/aqualon/product_data/brochures/250_10.pdf on Jul. 3, 2008, 30 pages, 1999.

Assouline, Michael et al, A Prospective Randomized Trial of Topical Soluble 0.1% Indomethacin Versus 0.1% Dislofenac Versus Placebo for the Control of Pain Following Excimer Laser Photorefractive Keratectomy, Ophthalmic Surgery Laser, 1998, 365-374, 29(5).

Banker, Gilbert et al, Ophthalmic Pharmaceutical Products, Modern Pharmaceutics, 4th ed., 2002, 12, 4th Edition, Marcel Dekker, Inc.

Bapatla, Krishna et al, Ophthalmic Ointments and Suspensions, Pharmaceutical Dosage Forms: Diperse Systems, 1989, 461-494, 2.

Boylan, J.C., Liquids, The Theory and Practice of Industrial Pharmacy, 1986, 457-478, 3rd Edition.

Burgalassi, Susi et al, Cytotoxicity of Potential Ocular Permeation Enhancers Evaluated on Rabbit and Human Corneal Epithelial Cell Lines, Toxicol. Lett., 2001, 1-8, 122(1).

Carter, S.J., 29: Ophthalmic Products, Cooper and Gunn's Dispensing for Pharmaceutical Students, 1975, 634-662, 12th Edition.

Cha, Seung-Heon et al, Corneal Epithelial Cellular Dysfunction From Benzalkonium Chloride (BAC) in vitro, Clinical and Experimental Opthalmology, 2004, 180-184, 32(2).

Chiambaretta, F. et al, Ocular Tolerance of a New Formulation of Nonpreserved Diclofenac, J. Fr. Ophthalmol., 2004, 739-744 (English Abstract), 27(7), Abstract only.

Donnenfeld, Eric et al, Double-Masked Study of the Effects of Nepafenac 0.1% and Ketorolac 0.4% on Corneal Epithelial Wound Healing and Pain After Photorefractive Keratectomy, Advances in Therapy, Jul. 1, 2007, 852-862, 24 (4).

Fielder, Michael, Clinical Implications of Ketorolac for Postoperative Analgesia, Journal of PeriAnesthesia Nursing, Dec. 1997, 426-433, 12(6).

Flach, AJ et al, The Effect of Ketorolac Tromethamine in Reducing Postoperative Inflammation: Double-Mask Parallel Comparison with Dexamethasone, Ann Ophthalmol, 1989, 407-411 (Abstract), 21(11).

Flach, Allan, Topically Applied Nonsteroidal Anti-inflammatory Drugs and Corneal Problems: An Interim Review and Comment, Ophthalmology, Jul. 2000, 1224-1226, 107(7).

Fodor, Anthony et al., Mechanism of Tetracaine Block of Cyclic Nucleotide-gated Channels, 1997, J. Gen. Physiol., Abstract printed from http://www.jpg.org/cgi/content/abstract/10911/3 on Jul. 4, 2008, vol. 109, No. 1, 3-14—Abstract only.

Furrer, Pascal et al, Ocular Tolerance of Absorption Enhancers in Ophthalmic Preparations, AAPS PharmSci, 2002, 1-5, 4(1).

Furrer, Pascal et al, Ocular Tolerance of Preservatives and Alternatives, European Journal of Pharmaceutics and Biopharmaceutics, 2002, 263-280, 53.

Garrett, Qian et al, Carboxymethyl Cellulose Stimulates Rabbit Corneal Epithelial Wound Healing, Current Eye Research, 2008, 567-573, 33 (7), Informa Healthcare.

Gaynes, Bruce et al, Topical Nonsteroidal Anti-Inflammatory Drugs for Ophthalmic Use: A Safety Review, Drug Safety, 2002, 233-250, 25(4).

Guidera, Ann et al, Keratitis, Ulceration, and Perforation Associated with Topical Nonsteroidal Anti-Inflammatory Drugs, The American Academy of Ophthalmology, 2001, 936-944, 108(5).

Hecht, Gerald, Ophthalmic Preparations, Remington: The Science and Practice of Pharmacy, 2000, 819-835, 20 edition.

Islam, MR, Citrate Can Effectively Replace Bicarbonate in Oral Rehydration Salts for Cholera and Infantile Diarrhoea, Bull World Health Organ., 1986, 145-150 (Abstract), 64(1).

Jaanus, Siret et al, Antiinflammatory Drugs, Clinical Ocular Pharmacology, 2001, 265-298.

Koay, Peter, The Emerging Roles of Topical Non-Steroidal Anti-Inflammatory Agents in Ophthalmology, Brit. J. Ophthalmology, 1996, 1117.

Kronemyer, Bob, Acular Reformulated to Reduce Ocular Pain, Burning, Stinging, Ocular Surgery News, Sep. 15, 2003, 48.

Kusano, Mao et al, Evaluation of Acute Corneal Barrier Change Induced by Topically Applied Preservatives Using Corneal Transepithelial Electric Resistance in Vivo, Cornea, 2010, 80-85, 29 (1).

Lamotte, Jo et al, The Effect of Artificial Tears With Different CMC Formulations on Contrast Sensitivity, ARVO Annual Meeting Abstract Search and Program Planner, 2002, Abstract No. 3151, 43.

Lee, Barry et al, Corneal Ulceration and Perforation With Ketorolac Tromethamine, Cornea, 2006, 1268, 25 (10).

Madhu, Cherukury et al, Effect of Benzalkonium Chloride/EDTA on the Ocular Bioavailability of Ketorolac Tromethamine Following Ocular Instillation to Normal and De-epithelialized Corneas of Rabbits, Journal of Pharmaceutical Sciences, Apr. 1996, 415-418, 85(4).

Malhotra, Manjusha et al, Effect of Preservative, Antioxidant and Viscolizing Agents on in Vitro Transcorneal Permeation of Ketorolac Tromethamine, Indian Journal of Experimental Biology, May 2002, 555-559, 40.

Malhotra, Manjusha et al, In Vivo Ocular Availability of Ketorolac Following Ocular Instillations of Aqueous, Oil, and Ointment Formulations to Normal Corneas of Rabbits: A Technical Note, AAPS PharmSciTech, 2005, E523-E526, 6(3).

Marsh, R.J., The Influence of Non-Ionic Detergents and Other Surfactants on Human Corneal Permeability, Exp. Eye Res., 1971, 43-48, 11.

Maurer, James et al, Ocular Irritation: Microscopic Changes Occurring Over Time in the Rat with Surfactants of Known Irritancy, Toxicologic Pathology, 1998, 217-225, 26(2).

Maurer, James et al, Ocular Irritation: Pathological Changes Occurring in the Rat with Surfactants of Unknown Irritancy, Toxicologic Pathology, 1998, 226-233, 26(2).

MayoClinic.com, Dry Eyes, Printed from http://www.mayoclinic.com/health/dry-eyes/DS00463/METHOD=print&DSECTION=all on Jul. 1, 2010, 14 pages.

(56) References Cited

OTHER PUBLICATIONS

MedlinePlus, U.S. National Library of Medicine and National Institutes of Health, Dry Eye Syndrome, Printed from http://www.nlm.nih.gov/medlineplus/ency/article1000426.htm on Jul. 1, 2010, 2 pages.

Missotten, Luc et al, Topical 0.1% Indomethacin Solution Versus Topical 0.1% Dexamethasone Solution in the Prevention of Inflammation After Cataract Surgery, Ophthalmologica, 2001, 43-50, 215.

Ophthalmic nonsteroidal Anti-Inflammatory Drugs (NSAIDs) Review, Sep. 2008, 8 pages, Provider Synergies.

Ophthalmic Ointments, 26 U.S. Pharmacopeia, 2003, 2183-2184.

Price, F. et al, Safety and Efficacy of Reformulated Ketorolac Tromethamine 0.4% Ophthalmic Solution in Post-Photorefractive Keratectomy Patients, Association for Research and Vision in Ophthalmology, Presented May 6, 2003, Poster 2611, 8:30am.

Rooks, W.H., The Analgesic and Anti-Inflammatory profile of Ketorolac and Its Tromethamine Salt, Drugs Exptl. Clin. Res., 1985, 479-492, XI(8).

Rooks, W.H., The Pharmacologic Activity of Ketorolac Tromethamine, Pharmacotherapy, 1990, 30S-32S, 10(Supp 6).

Rossi, S. et al., Drug Release and Washability of Mucoadhesive Gels Based on Sodium Carboxymethylcellulose and Polyacrylic Acid, Pharmaceutical Development and Technology, 1999, 55-63, 4 (1), US.

Rowe, Raymond et al, Sodium Citrate Dihydrate, Handbook of Pharmaceutical Excipients, 2006, 675-677, 5th Edition, Pharmaceutical Press.

Rowland, Malcolm et al, Clinical Pharmacokinetics: Concepts and Applications, 1995, 61, 3.

Ruggiero, Ronald, Prescription Contraceptives: Countering the Risks, American Pharmacy, Sep. 1985, 32-37, NS25(9).

Sandoval, Helga et al, Evaluation of 0.4% Ketorolac Tromethamine Ophthalmic Solution Versus 0.5% Ketorolac Tromethamine Ophthalmic Solution After Phacoemulsification and Intraocular Lens Implantation, Journal of Ocular Pharmacology and Therapeutics, 2006, 251-257, 22(4).

Sasaki, Hitoshi et al, Ophthalmic Preservatives As Absorption Promoters for Ocular Drug Delivery, J. Pharm. Pharmacol., 1995, 703-707, 47, US.

Sheppard, John, Using NSAIDs to Full Potential: Expert Guidance on Maximizing Utility, Ophthalmology MGMT, Nov. 2001, 3 pages.

Simmons, Peter, Refresh Liquigel™ : A New Approach to the Treatment of Persistent Dry Eye, Therapeutic Reporter, 2002, 68-71, 13(2).

Solomon, KD et al, Topical Ketorolac Tromethamine 0.5% Ophthalmic Solution in Ocular Inflammation After Cataract Surgery, Ophthalmology, Feb. 2001, 331-7 (Abstract Only) 2 Pages, 108(2).

Solomon, Kerry et al, Comparison of Ketorolac Tromethamine 0.5% and Rimexolone 1% to Control Inflammation After Cataract Extraction, J Cataract Refract Surg, 2001, 1232-1237, 27.

Solomon, Kerry et al, Safety and Efficacy of Ketorolac Tromethamine 0.4% Ophthalmic Solution in Post-Photorefractive Keratectomy Patients, J Cataract Refract Surg, Aug. 2004, 1653-1660, 30.

South African Electronic Package Inserts (Retrieved on Feb. 3, 2012 from the Internet<URL:http://www.home.intekom.com/pjarm/allergan/refre-tr.html, published on Nov. 2004).

Stahl, Heinrich et al, Handbook of Pharmaceutical Salts: Properties, Selection, and Use, 2002, 324-325, International Union of Pure and Applied Chemistry.

Teal, Patricia et al, Corneal Subepithelial Infiltrates Following Excimer Laser Photorefractive Keratectomy, J Cataract Refract Surg, 1995, 516-518, 21(5).

The Cosmetic Ingredient Review Expert Panel, Safety Assessment of Salicyclic Acid, Butyloctyl Salicylate, Calcium Salicylate, C12-15 Alky Salicylate, Capryloyl Salicylic Acid, Hexyldodecyl Salicylate, Isocetyl Salicylate, Isodecyl Salicylate, Magnesium Salicylate, MEA- Salicylate, Ethylhexyl Salicylate, Potassium Salicylate, Methyl Salicylate, Myristy Salicylate, Sodium Salicylate, Tea— Salicylate, and Tridecyl Salicylate, Cosmetic Ingredient Review, 2003, 1-108, 22(Suppl. 3).

The United States Pharmacopeia, Antimicrobial Effectiveness Testing, The United States Pharmacopeia, Jan. 1, 2003, 2002-2004, 26th Edition, US.

Thomas Abrams, Warning Letter, May 25, 2007, 7 pages, Food and Drug Administration, Rockville, MD.

Tutton, Miles et al, Efficacy and Safety of Topical Diclofenac in Reducing Ocular Pain After Excimer Photorefractive Keratectomy, J Cataract Refract Surg, Jun. 1996, 536, 22(5).

U.S. Appl. No. 60/478,713, filed Jun. 13, 2003.

UIC Department of Ophthalmology and Visual Sciences, Dry Eyes, Printed from http://www.uic.edu/com/eye/learningaboutvision/eyefacts/dryeyes.shtml on Jul. 1, 2010, 6 pages.

Waterbury, David et al, Comparison of Ketorolac Tromethamine, Diclofenac Sodium, and Loteprednol Etabonate in an Animal Model of Ocular Inflammation, Journal of Ocular Pharmacology and Therapeutics, 2006, 155-159, 22(3).

Waterbury, David et al, Efficacy of Low Concentrations of Ketorolac Tromethamine in Animal Models of Ocular Inflammation, Journal of Ocular Pharmacology and Therapeutics, 2004, 345-352, 20(4).

Whittpenn, John, Acular LS: Reduced Discomfort without Loss of Efficiency, Ophthalmology Management, Aug. 2003, 12-15, 7(Suppl 8).

www.rxlist.com, Alcaine-Clinical Pharmacology, http://www.rxlist.com/cgi/generic/propara_cp.htm, printed Jul. 4, 2008, 2 pages.

Xu, Keping, Ex vivo corneal Epithelial wound healing following exposure to ophthalmic nonsteroidal anti-inflammatory drugs, Clinical Ophthalmology, 2011, 269-274, 5(1).

* cited by examiner

COMPOSITIONS FOR DELIVERY OF THERAPEUTICS INTO THE EYES AND METHODS FOR MAKING AND USING SAME

RELATED APPLICATION

This application is a continuation of U.S. patent application Ser. No. 10/911,966, filed Aug. 5, 2004, which is a Non-Provisional of U.S. Provisional Patent Application Ser. No. 60/493,178, filed Aug. 7, 2003, and U.S. Provisional Patent Application Ser. No. 60/493,188, filed Aug. 7, 2003, the disclosures of which are hereby incorporated in their entirety herein by reference.

BACKGROUND OF THE INVENTION

The present invention relates to compositions and methods useful for administering a therapeutic component to a human or animal. More particularly, the present invention relates to compositions and methods which are very effective in facilitating administration of medication through a cornea of an eye.

Prior art compositions useful for administering medications into the eyes are generally effective, although they often have certain shortcomings. For example, these compositions typically require relatively frequent administration and/or relatively high concentration of the medication since they are often rapidly washed away by the natural processes of the eye. Frequent administration and/or high concentration of a medication may contribute to certain unwanted side effects.

There remains a need for new compositions which provide effective and/or efficient delivery of medications, such as therapeutics, into and/or through the eyes that can be conveniently used, for example, periodically administered over acceptably long intervals of time and/or at reduced therapeutic component concentrations.

SUMMARY OF THE INVENTION

New compositions for administering therapeutic components, and methods for using such compositions, have been discovered. These compositions are relatively straightforward, can be easily and cost effectively manufactured and can be used for effectively and/or efficiently administering of therapeutic components to or through the eyes. Importantly, the present compositions include materials which preferably provide for delivery of the therapeutic components into the eye, for example, through the cornea of the eye, often without the need for frequent readministration or replenishment. In addition, the present compositions are advantageously not unduly disruptive to clear vision of the eyes to which the compositions are administered.

In one broad aspect, the present invention is directed to compositions comprising a retention component, a therapeutic component, for example, a therapeutically effective amount of a therapeutic component, and an ophthalmically acceptable carrier component.

The retention component is advantageously effective to provide the compositions of the invention with, for example, an increased retention to or on the cornea of an eye when applied to the eye relative to substantially identical compositions without the retention component. The increased retention to or on the cornea provides for, for example, an increased penetration of the therapeutic component through the cornea and into the eye. Compositions of the present invention may be employed in methods which comprise administering the composition to a cornea of an eye, for example, contacting the composition with the cornea of the eye.

When included in compositions of the present invention, the retention component is effective to provide the compositions with one or more of the following: 1) a reduced wettability of the composition, for example, to human skin (e.g., a lower dermal eyelid) and/or cilia, for example, eye lashes, relative to a substantially identical composition without the retention component; 2) an increased meniscus height on a cornea of an eye relative to a substantially identical composition without the retention component and/or an increase in the time whereby meniscus height is increased on a cornea of an eye relative to a substantially identical composition without the retention component; 3) an increased muco-adhesion of the composition relative to a substantially identical composition without the retention component; 4) an increased or even substantially optimized, as described elsewhere herein, viscosity of the composition relative to a substantially identical composition without the retention component; and 5) an increased physical apposition or layering, for example, an increased tear thickness, on the cornea of an eye relative to a substantially identical composition without the retention component.

The present compositions may have a wettability less than or equal to that of human tear fluid. In one embodiment, the present compositions have a wettability less than saline containing about 0.1% (w/v) to about 2.0% (w/v) hydroxypropyl methylcellulose, for example, about 0.2% (w/v) to about 1.0% (w/v) hydroxypropyl methylcellulose or about 0.5% (w/v) hydroxypropyl methylcellulose. In another embodiment, the present compositions have a wettability less than saline containing 0.5% (w/v) carboxymethylcellulose having an average molecular weight of 90,000.

Reduced wettability of the compositions may be due, at least in part, to an increase in surface tension of the compositions, for example, an increase in surface tension of the compositions relative to human tears or human tear fluid. Surface tension measurements of the present compositions may range from about 10 dynes to about 300 dynes, for example, from about 60 dynes to about 75 dynes.

The present compositions may have a surface tension greater than or equal to human tear fluid. In addition, the compositions may have an advancing contact angle, as measured on human skin or a similar surface, greater than or equal to human tear fluid. In one embodiment, the present compositions have a surface tension greater than saline containing about 0.1% (w/v) to about 2.0% (w/v) hydroxypropyl methylcellulose, for example, about 0.2% (w/v) to about 1.0% (w/v) hydroxypropyl methylcellulose, or about 0.5% (w/v) hydroxypropyl methylcellulose. In another embodiment, the present compositions have a surface tension greater than saline containing 0.5% (w/v) carboxymethylcellulose having an average molecular weight of 90,000. In one embodiment, the present compositions have an advancing contact angle greater than saline containing about 0.1% (w/v) to about 2.0% (w/v) hydroxypropyl methylcellulose, for example, about 0.2% (w/v) to about 1.0% (w/v) hydroxypropyl methylcellulose, or about 0.5% (w/v) hydroxypropyl methylcellulose. In another embodiment, the compositions have an advancing contact angle greater than saline containing 0.5% (w/v) carboxymethylcellulose having an average molecular weight of 90,000.

The retention component at a concentration present in the composition may be substantially ineffective to reduce human tear fluid surface tension, for example, when mixed on the eye with tear fluid. In one embodiment, the retention component, at a concentration present in the composition, is effective to increase human tear fluid surface tension, for example, when mixed on the eye with tear fluid.

In one embodiment, the present compositions are substantially ineffective to wet the dermal portion of the eyelid of a human eye after the composition is administered to the human eye. For example, the present compositions may be substantially ineffective to wet a portion of the eyelid external to the lid margin or muco-cutaneous junction, that is, the junction between the conjunctiva mucus membrane tissue and the dermis of the eyelid.

Compositions of the invention including a retention component preferably have an increased meniscus height on the cornea of an eye when applied to the eye relative to substantially identical compositions without the retention component. The meniscus height of a composition of the invention may be increased by an amount in a range of about 1% to about 5,000% or more, for example, in a range of about 10% to about 2,000%, relative to the meniscus height on the cornea of an eye of a substantially identical composition which does not include a retention component. In one embodiment, the meniscus height of a composition of the invention is increased by an amount in a range of about 10% or about 20% to about 400% or about 500% or about 1,000% relative to the meniscus height on the cornea of an eye of a substantially identical composition which does not include a retention component.

When applied to the eyes, for example, human eyes, the present compositions preferably will have a meniscus height on the cornea greater than or equal to the meniscus height of human tear fluid. In one embodiment, when applied to the eyes, the present compositions have a greater meniscus height on the cornea than saline containing about 0.1% (w/v) to about 2.0% (w/v) hydroxypropyl methylcellulose, for example, about 0.2% (w/v) to about 1.0% (w/v) hydroxypropyl methylcellulose, or about 0.5% (w/v) hydroxypropyl methylcellulose. In another embodiment, when applied to the eyes, the present compositions have a greater meniscus height on the cornea than saline containing 0.5% (w/v) carboxymethylcellulose having an average molecular weight of 90,000.

Muco-adhesion can be defined as the adhesion of a substance, for example, an ophthalmic composition, to a surface, for example, a corneal surface or the surface of the cornea of an eye.

The present compositions may have a muco-adhesion greater than or equal to human tear fluid. In one embodiment, the present compositions have a muco-adhesion greater than the muco-adhesion of saline containing 0.5% (w/v) carboxymethylcellulose having an average molecular weight of 90,000.

The present compositions may have a viscosity greater than or equal to human tear fluid. In one embodiment, the present compositions have a viscosity greater than saline containing 0.5% (w/v) carboxymethylcellulose having an average molecular weight of 90,000. The viscosity of compositions of the invention may be in a range of about 1 cps to about 10,000 cps with a shear rate in a range of about 0.5 per second to about 10 per second, for example, about 2 cps to about 5000 cps with a shear rate in a range of about 0.5 per second to about 10 per second. In one embodiment, the viscosity of compositions of the invention may be in a range of about 5 cps to about 500 cps with a shear rate in a range of about 0.5 per second to about 10 per second, for example, about 20 cps to about 100 cps with a shear rate in a range of about 1 per second to about 5 per second, for example, about 2 per second. In one embodiment, the retention component is effective to provide the composition with a viscosity greater than about 40 cps at 35° C., the composition having a shear rate of about 2 per second.

Compositions of the invention may be shear thinning or substantially non-shear thinning.

Although the present compositions may have a somewhat increased viscosity, consideration advantageously should be given to limit the viscosity of the present compositions to avoid the composition being excluded or removed from the eye by the mechanical action of the eyelid. In one particularly useful embodiment of the present invention, the compositions have a reduced viscosity relative to a substantially identical composition which has sufficient viscosity to be substantially excluded from an eye by a mechanical action of an eye lid of the eye after the substantially identical composition is administered to the eye.

Compositions of the invention including a retention component may have an increased physical apposition or layering on the cornea of an eye relative to a substantially identical composition without the retention component. In one embodiment, an increased physical apposition is characterized by an increased meniscus height and a reduced wettability of a liquid composition, for example, a composition of the invention. The increased physical apposition of the present compositions may be a result of the increased meniscus height and the reduced wettability of the present compositions.

The present compositions may have a physical apposition greater than or equal to that of human tear fluid. In one embodiment, the present compositions have a physical apposition greater than saline containing 0.5% (w/v) carboxymethylcellulose having an average molecular weight of 90,000.

Without wishing to limit the invention to any theory of operation, the function of the retention components may be facilitated by the electrical charge of the present compositions.

Any suitable retention component capable of functioning as such may be employed in the present invention. The retention component should have no undue detrimental effect on the eye to which the composition is administered, on the human or animal to whom the composition is being administered, or on the composition itself. The retention components preferably are ophthalmically acceptable in the present compositions. The retention component may include, for example, and without limitation, a polyanionic component. In one embodiment, the retention component, e.g., polyanionic component, is present in an amount of at least about 0.01% (w/v) of the composition. For example, the retention component may be present in an amount in a range of about 0.05% (w/v) or about 0.1% (w/v) to about 60% (w/v) or about 0.1% (w/v) to about 10% (w/v) or about 20% (w/v). In another example, the retention component is present in an amount in a range of about 0.05% (w/v) or about 0.1% (w/v) to about 5% (w/v), for example, about 0.2% (w/v) to about 5% (w/v). In another example the retention component is present in an amount in a range of about 0.6% to about 1.8% (w/v).

The polyanionic component may include one or more polyanionic component portions, for example, two, three, four, five, six, seven, eight, nine, ten, eleven, twelve, thirteen, fourteen, fifteen, sixteen, seventeen, eighteen, nineteen, twenty or more polyanionic component portions. In one embodiment, each polyanionic component portion has a molecular weight different from another polyanionic component portion in a composition.

Average molecular weights of polyanionic component portions of the invention may be about 5,000 or less or about 10,000 or more. In one embodiment, the molecular weights of polyanionic component portions are about 5,000 to about 10,000,000, for example, about 10,000 or about 20,000 to about 2,000,000 or about 5,000,000.

In one very useful embodiment, the polyanionic component includes a first polyanionic component portion having a first molecular weight, and a second polyanionic component having a second, preferably different, molecular weight. Advantageously each of the polyanionic component portions may be present in an amount effective to provide an enhanced delivery of a therapeutic component to a patient, for example, to an eye of a patient, when administered to the patient, for example, when administered to a cornea of a patient, relative to a substantially identical composition with no first polyanionic component portion. Such a composition may be administered by contacting the composition with the cornea of an eye.

In one embodiment, each polyanionic component portion is present in an amount of at least about 0.01% (w/v) of the composition. For example, each of the polyanionic component portions may be present in an amount in a range of about 0.01% (w/v) to about 60% (w/v), for example, about 0.01% (w/v) to about 10% (w/v) to about 20% (w/v). In another example, each of the polyanionic component portions is present in an amount in a range of about 0.2% (w/v) or about 0.1% (w/v) to about 5% (w/v). In a further example, each of the polyanionic component portions is present in an amount in a range of about 0.1% (w/v) to about 2.0% (w/v).

As noted above, each of the polyanionic component portions may have a different molecular weight. In one embodiment, the first polyanionic component portion has a first molecular weight which is greater than the second molecular weight of the second polyanionic component portion. The difference in molecular weight between the polyanionic component portions, for example, between the first molecular weight of the first polyanionic component portion and the second molecular weight of second polyanionic component portion, may be at least about 5,000 or at least about 10,000, for example, at least about 50,000. In one embodiment, the difference in molecular weight between the polyanionic component portions, for example, between the first molecular weight of the first polyanionic component portion and the second molecular weight of second polyanionic component portion, is between about 5,000 and about 10,000,000.

In one embodiment, the weight ratio of the first polyanionic component portion and the second polyanionic component portion is in a range of about 0.02 to about 50. For example, the weight ratio of the first polyanionic component portion and the second polyanionic component portion may be in a range of about 0.25 to about 4.

As used herein the term "molecular weight" refers to weight average molecular weight, as that term is commonly known within the polymer art, and can be measured or determined using procedures and/or techniques well known in the polymer art.

Any suitable polyanionic component may be employed in accordance with the present invention. Such polyanionic component should be ophthalmically acceptable in the present compositions, compatible with the other components of the composition, and effective, in ophthalmically reasonable concentrations, to facilitate administration of a therapeutic component to a patient when administered to an eye of the patient and to otherwise function in accordance with the present invention.

In one useful embodiment, the polyanionic component is selected from anionic cellulosic derivatives and mixtures thereof. In one embodiment, when two or more polyanionic component portions are employed, one or more, for example, all, of the polyanionic component portions of the present compositions are selected from anionic cellulosic derivatives and mixtures thereof. In one useful embodiment, the polyanionic component or all of the polyanionic component portions are carboxymethylcelluloses or mixtures thereof.

Other suitable polyanionic components or polyanionic component portions include anionic homopolymers and copolymers which include units of one or more of acrylic acid, methacrylic acid, metal acrylates and metal methacrylates or mixtures thereof. For example, useful polyanionic component or polyanionic component portions include homopolymers and copolymers comprising units of one or more of acrylic acid, metal acrylates or mixtures thereof.

Any suitable therapeutic component may be included in, and delivered by, the present compositions. Advantageously, the therapeutic component in the present compositions is at least compatible with ocular tissue, and preferably is ophthalmically acceptable. The therapeutic component may be such as to provide a desired therapeutic effect to the eye and/or to another body part and/or systemically to the human or animal to whom the present composition is administered.

Since the present compositions allow for much more of the therapeutic component that is administered to the eye to actually pass through, or penetrate the cornea, rather than being washed away by the natural processes of the eye, the present compositions may, and preferably do, include a reduced quantity of the therapeutic component in a composition to obtain a given therapeutic effect relative to a substantially identical composition having no retention component. One benefit of this feature is the ability to reduce potential side effects, for example, allergy side effects, of the therapeutic component while maintaining efficacy. Alternatively, the present compositions can provide an enhanced therapeutic effect with the same concentration of therapeutic component, for example, relative to substantially identical compositions having no retention component. In general, the present compositions provide for more effective utilization of the therapeutic component relative to substantially identical compositions having no retention component.

In addition to being useful for administering therapeutic components to a the eye of a patient, or to a patient through the eye of the patient, the present compositions can be effective to provide lubrication to an eye when administered to the eye, for example, when administered to the cornea of the eye. In one embodiment, the present compositions are effective to administer therapeutic components to a patient, for example, to the eye of a patient and are effective to provide lubrication to the eye when administered to the eye, for example, when administered to the cornea of the eye.

The carrier component is ophthalmically acceptable and may include one or more components which are effective in providing such ophthalmic acceptability and/or otherwise benefiting the composition and/or the eye to which the composition is administered and/or the patient whose eye the composition is administered to. Advantageously, the carrier component is aqueous-based, for example, comprising a major amount, that is at least about 50% by weight, of water.

Methods of producing the present compositions may include contacting or combining the retention component with the ophthalmically acceptable carrier component and the therapeutic component. The present compositions may be prepared using conventional procedures and techniques. For example, the present compositions can be prepared by blending the components together.

The present compositions can be solutions, although other forms, such as ointments, gels, creams, emulsions and the like may be employed.

The present invention also provides for methods of administering the compositions. These methods may include contacting a composition of the invention with a cornea of an eye. More particularly, a therapeutic component may be administered to a patient by contacting the present compositions which comprise a therapeutic component with the cornea of an eye. The present administering step can be repeated at least once, and preferably as needed to effectively treat the eye to which the composition is administered.

In one very useful embodiment, the eye to which the composition is administered has an increased intraocular pressure relative to a normal eye or has a propensity toward increased intraocular pressure. In one embodiment, the compositions are effective to reduce the intraocular pressure of an eye when the compositions are administered to the eye.

Commonly assigned U.S. patent application Ser. No. 09/848,249, filed May 3, 2001, U.S. patent application Ser. No. 09/847,935 filed May 3, 2001, U.S. patent application Ser. No. 10/136,240, filed May 1, 2002 and application Ser. No. 10/017,817, filed Dec. 14, 2001 are directed to subject matter somewhat related to the present patent application. The disclosure of each of these co-pending U.S. patent applications is incorporated in its entirety herein by reference.

Each and every feature described herein, and each and every combination of two or more of such features, is included within the scope of the present invention provided that the features included in such a combination are not mutually inconsistent.

These and other aspects and advantages of the present invention are apparent in the following drawings, detailed description, examples and claims.

DETAILED DESCRIPTION

Figure 1A:
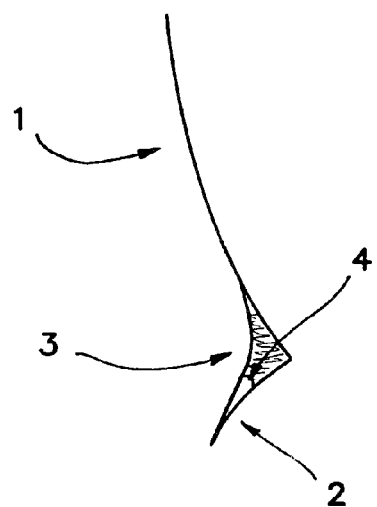
FIG. 1A shows the contact angle of a composition of Example 1 which includes hydroxypropyl methyl cellulose (HPMC) in place of high molecular weight carboxymethyl cellulose (HCMC) and medium molecular weight carboxymethyl cellulose (MCMC).

The present invention provides for compositions which are advantageously ophthalmically acceptable comprising a retention component, a therapeutic component and an ophthalmically acceptable carrier component. The present compositions provide for an increased penetration of therapeutic components through the cornea of an eye relative to an identical composition without the retention component.

It is discovered that the total volume of composition that can be placed on the eye without spillover after the drop is first applied and/or retention over time of the composition to an ocular surface after the initial application period are important factors for efficient delivery of a therapeutic component to the eyes.

Composition wettability, meniscus height on a cornea of an eye, muco-adhesion, viscosity, physical apposition or layering on a cornea are factors which influence the total volume of a composition that may be retained on the ocular surface during and/or after the initial period after administration of a composition to an eye. The present invention provides for compositions which include a retention component which is effective to provide an increased total volume of a composition to be retained on the ocular surface during and/or after the initial period after administration of the composition to an eye by providing the present compositions with one or more of: a reduced wettability, an increased meniscus height on the cornea of the eye, an increased muco-adhesion, an increased or substantially optimized viscosity and an increased physical apposition or layering on a cornea of an eye. This increased total volume of a composition to be retained on the ocular surface facilitates penetration of the therapeutic component through the cornea of the eye to which the composition is applied.

The volume of a single eye drop (about 40-50 microliters) generally exceeds the total tear volume that is on the ocular surface prior to application. This surge in volume produced by an eye drop may exceed the tear "holding capacity" of an eye resulting in an excess of composition which spills over the lid or exits at the nasal or temporal canthi. Human tear fluid as secreted has a surface tension of about 40 dynes/cm which is lower than water, which is about 70 dynes/cm, making the tear fluid able to wet the ocular surface effectively. In addition, this low surface tension allows tears to wet the periocular skin effectively which leads to visible drainage of the tears, or tearing, away from the ocular surface onto the skin.

In one embodiment, when a composition of the present invention is applied to the ocular surface, the resultant mixture of tear volume and composition results in a surface tension above that of tears. In this embodiment, the mixture is not effective to wet the skin, for example, the periocular skin.

It is demonstrated in the present invention that when administering a therapeutic component to an eye, it is advantageous to place and retain a maximum volume of medication on the ocular surface for a prolonged period of time in order to allow for maximum delivery of the therapeutic component into the eye.

In one embodiment, the present invention provides for the presence of a large volume of a composition on an eye during the initial period after application of the composition to the eye allowing for a facilitated delivery of therapeutic component into the eye. In one embodiment, the initial period after application of the composition to the eye is in a range of about 1 second to about 10 seconds or about 30 seconds or about 1 minute.

Viscosity of a composition is one factor in determining the volume of composition retained on the eye over time. The relation of viscosity to total initial volume retained on the ocular surface of the eye after one or more blinks of the eye may be non-linear and can be described as an inverted "U" shape. That is, when a very high viscosity composition is placed on the ocular surface, it can be partially expelled due to action of the eye lids whereby the lid margin physically pushes the composition from the ocular surface onto the eye lashes and/or periocular skin. In addition, low viscosity compositions can readily exit the ocular surface by drainage, for example, through the inferior and superior puncta. Therefore, in one embodiment, the present invention provides for compositions with an optimum viscosity which maximizes retention of composition to the eye after application of the composition to the eye.

Muco-adhesion of a composition can affect retention of a composition to an ocular surface. The present invention contemplates compositions which preferably include a muco-adhesive component allowing for adhesion of the composition to an eye. Muco-adhesive components include, for example, substances which are negatively charged.

In one embodiment, the presence of a large volume of a composition on an ocular surface during the initial period after application of the composition to the eye may be particularly useful for the efficient penetration of therapeutics into a patient, for example, into an eye of the patient, by passing through, for example, the cornea. In another embodiment, the retention over time of a composition on the ocular surface may be particularly useful for the efficient penetration of therapeutics into an eye of the patient, bypassing through, for example, the cornea. In one embodiment, the molecular weight and/or charge of the therapeutic component may determine if efficient penetration of the therapeutic component into an eye of the patient, by passing through, for example, the cornea, is preferably facilitated by the presence of a large volume of a composition on an ocular surface during the initial period after application of the composition to the eye or by the retention over time of the composition on the ocular surface.

Without wishing to limit the present invention to any theory of operation, it is thought that a therapeutic component included in the present compositions migrates into the eye in a manner which allows for an increased percentage of therapeutic component to be delivered into the eye per unit volume of composition administered to the eye relative to an equal volume of a substantially identical composition without a component, such as the present retention component, which provides for one or more of a decreased wettability, an increased, for example, substantially optimum, viscosity, an increased muco-adhesion, an increased meniscus height on a cornea of an eye and/or an increased physical apposition to a cornea of an eye.

By increasing the amount of therapeutic component delivered into the eye of a patient, the present compositions allow for a significantly lower concentration of therapeutic component to be included in a composition to achieve the same or similar beneficial effect to a patient. Additionally or alternatively, a less frequent administration of a composition may be used to attain the same or similar beneficial effect.

In one embodiment, the present compositions allow for a larger volume of composition with a reduced therapeutic component concentration to be applied to the eye resulting in an equal amount of therapeutic component penetrating the cornea relative to compositions which do not include a retention component and have a higher concentration of therapeutic component.

Without wishing to limit the invention to any particular theory of operation, it is believed that the present compositions are effective to increase physical apposition of a composition to the cornea of an eye relative to a substantially identical composition having no retention component. For example, the composition when administered to the eye is believed to form a layer on the eye covering a portion of the cornea, for example, a lower portion of the cornea. This layer may be formed at least in part by one or both of an increased meniscus height of the composition on the cornea of the eye and a reduced eyelid wettability of the composition, each of said increased height and reduced wettability being relative to a substantially identical composition having no retention component.

The layer formed by the composition on the cornea allows for an increased amount of composition containing therapeutic component to be present on the cornea. The layer formed on the cornea may also provide for a longer time interval in which the composition is retained on the cornea. Ultimately, the increased amount of composition on the cornea and/or the longer time interval in which the composition is retained on the cornea results in an increased amount of therapeutic component passing through the cornea before the composition is washed away by the natural processes of the eye, relative to a composition that does not form such a layer.

In one embodiment, the invention contemplates the delivery of the therapeutic component primarily through the cornea of an eye into the eye as opposed to delivery of the therapeutic component through the conjunctiva or sclera of an eye into the eye.

Without wishing to limit the invention to any theory of operation, is believed that the reason why the cornea is a particularly favorable target for therapeutic component delivery enhancement is because retention of a composition of the invention on the cornea is facilitated by the action of the eye lid during a blink. For example, during the blink of an eye, the eyelid moves down distributing fluid across the cornea. Upon brief lid closure that occurs during a blink, mixing of tears with a composition that has been administered to the eyes occurs. When the lid is opened, the tear/composition mixture is pulled upward across the cornea allowing for the composition to be retained on the cornea.

Retention components included in the present compositions advantageously are useful to provide for one or more of a reduced wettability, an increased viscosity, an increased muco-adhesion, an increased meniscus height on a cornea of an eye and an increased physical apposition or layering to a cornea of an eye.

The present invention also contemplates retention components which include mixtures of substances which, when the retention component is included in a composition, provide a composition with one or more of a reduced wettability, an increased viscosity, an increased muco-adhesion, an increased meniscus height on a cornea of an eye and an increased physical apposition or layering on a cornea of an eye relative to a substantially identical composition without the retention component.

Any suitable retention component can be employed in accordance with the present invention provided that it functions as described herein and has no substantial detrimental effect on the composition as a whole or on the eye to which the composition is administered. The retention component preferably is ophthalmically acceptable at the concentrations used.

In a very useful embodiment, the retention component is selected from polyanionic components and mixtures thereof. The polyanionic component can include, for example, and without limitation, two, three or more anionic, or negative, charges. Particularly useful anionic components are those which are water soluble, for example, soluble at the concentrations used in the present compositions at ambient or room temperature.

As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from the group consisting of polymeric materials having multiple anionic charges and mixtures thereof.

A useful class of polyanionic components are one or more polymeric materials having multiple anionic charges. Examples include, but are not limited to
    metal carboxymethylcelluloses
    metal carboxy methylhydroxyethylcelluloses
    metal carboxy methylstarchs
    metal carboxy methylhydroxyethylstarchs
    ammonium methylcelluloses
    amino compound methylcelluloses
    hydrolyzed polyacrylamides and polyacrylonitriles heparin
gucoaminoglycans
hyaluronic acid
chondroitin sulfate
dermatan sulfate
peptides and polypeptides
alginic acid
metal alginates
homopolymers and copolymers of one or more of:
  acrylic and methacrylic acids
  metal acrylates and methacrylates
  vinylsulfonic acid
  metal vinylsulfonate
  amino acids, such as aspartic acid, glutamic acid and the like
  metal salts of amino acids
  p-styrenesulfonic acid
  metal p-styrenesulfonate
  2-methacryloyloxyethylsulfonic acids
  metal 2-methacryloyloxethylsulfonates
  3-methacryloyloxy-2-hydroxypropylsulonic acids
  metal 3-methacryloyloxy-2-hydroxypropylsulfonates
  2-acrylamido-2-methylpropanesulfonic acids
  metal 2-acrylamido-2-methylpropanesulfonates allylsulfonic acid
  metal allylsulfonate and the like.

Polyanionic components useful in the present invention include those selected from carboxymethylcelluloses and mixtures thereof, for example, alkali metal and/or alkaline earth metal carboxymethylcelluloses. Other useful polyanionic components include polyacrylic acids, carbomer, carbopol, glucosaminoglycans, polycarbophil, specifically modified celluloses, native or modified gum substances such as alginates and caragenans, and the like and mixtures thereof.

Examples of suitable polyanionic components useful in the present compositions include, without limitation, anionic cellulose derivatives, anionic acrylic acid-containing polymers, anionic methacrylic acid-containing polymers, anionic amino acid-containing polymers and the like and mixtures thereof. Anionic cellulose derivatives are particularly useful in the present invention.

In one very useful embodiment, the polyanionic component includes a first polyanionic component portion having a first molecular weight; and a second polyanionic component having a second molecular weight. Advantageously, each of the polyanionic component portions is present in an amount effective to facilitate administration of the therapeutic component into the eye through the cornea of the eye when the composition is administered to the eye. Each of the polyanionic component portions can be present in an amount of at least about 0.1% (w/v) of the composition.

In one embodiment, the at least two polyanionic component portions, for example, the first and second polyanionic component portions, other than having different molecular weights, have substantially similar chemical structures. However, the at least two polyanionic component portions can have different chemical structures.

Each of the polyanionic component portions, for example, the first and second polyanionic component portions, can be separately derived. In other words, each of the polyanionic component portions can be combined into the present compositions as separate materials.

The present compositions preferably have viscosities in excess of the viscosity of water. In one embodiment, the viscosity of the present compositions is at least about 15 cps (centipoise), for example, in a range of about 15 cps to about 2000 cps or about 3,000 cps. Advantageously, the viscosity of the present composition may be in a range of about 30 cps or about 70 cps to about 750 cps or about 1000 cps. In one embodiment, the viscosity of a composition is a range of about 15 cps or about 50 cps to about 200 cps. In another embodiment, the viscosity of a composition is in a range of about 30 cps to about 5000 cps or about 200 cps to about 4000 cps. In still another embodiment, the viscosity of a composition is in a range of about 200 cps to about 2000 cps. The viscosities may be measured at a shear rate of between about 1 and about 10 per second.

The viscosity of the present compositions can be measured in any suitable manner. A conventional Brookfield viscometer can be used to measure such viscosities. The compositions can be either Newtonian or non-Newtonian compositions. Shear-thinning characteristics of non-Newtonian compositions that result in the composition having a lower viscosity under conditions of physical shear, for example, blinking, may allow for a higher initial viscosity for non-Newtonian compositions than Newtonian compositions.

As noted previously, each of the polyanionic component portions, that is, for example, at least the first and second polyanionic component portions, can be present in an amount of at least about 0.1% (w/v) of the composition. In one very useful embodiment, the polyanionic component is present in an amount in a range of about 0.2% (w/v) to about 5% (w/v), for example, about 0.4% (w/v) to about 2.5% (w/v), or for example, about 0.6% (w/v) to about 1.8% (w/v) or for example, about 0.8% (w/v) to about 1.3% (w/v) of the composition.

The weight ratio of the first polyanionic component portion to the second polyanionic component portion may vary over a wide range. In one embodiment, the ratio weight of the first portion to the second portion is in the range of about 0.02 to about 50, preferably about 0.1 to about 10, and more preferably about 0.25 to about 4.

The different, for example, first and second, polyanionic component portions of the present compositions may be separately derived. Put another way, the different, for example, first and second, polyanionic component portions can be blended into the present compositions from different sources. The molecular weights of the different polyanionic component portions can differ by at least about 10,000, for example, at least about 50,000.

The polyanionic component may further comprise a third polyanionic component portion having a third molecular weight which is different from the first and second molecular weights. The third polyanionic component portion may be present in an amount effective to facilitate administration of a therapeutic component, for example, a brimonidine component, to an eye relative to a substantially identical composition with no third polymeric component portion.

The present compositions may provide for enhanced therapeutic component delivery relative to a substantially identical composition having an equal total amount of the polyanionic component and substantially no first polyanionic component portion.

As noted elsewhere herein, any suitable therapeutic component may be employed in the present compositions. In one very useful embodiment, the therapeutic component may include a substance which is effective to decrease intraocular pressure when applied to the eyes.

The therapeutic component may include, without limitation, one or more of the following: NMDA antagonists; antibacterial substances such as beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides, aminoglycoside antibiotics such as gentamycin, kanamycin, amikacin, sisomicin and tobramycin; nalidixic acid and its analogs such as norfloxacin and the antimicrobial combination fluoroalanine/pentizidone, nitrofurazones and analogs thereof; antihistaminics and decongestants such as pyrilamine, chlorpheniramine, tetrahydrazoline, antazoline and analogs thereof; mast-cell inhibitors of histamine release, such as cromolyn; anti-inflammatories such as cortisone, hydrocortisone, hydrocortisone esters, betamethasone, dexamethasone, dexamethasone sodium phosphate, prednisone, methylprednisolone, medrysone, fluorometholone, prednisolone, prednisolone sodium phosphate, triamcinolone, indainethacin, sulindac, its salts and its corresponding sulfides, and analogs thereof; miotics and anticholinergics such as echothiophate, pilocarpine, physostigmine salicylate, diisopropylfluorophosphate, epinephrine, dipivaloylepinephrine, neostigmine echothiopate iodide, demecarim bromide, carbamoyl choline chloride, methacholine, bethanechol, and analogs thereof; mydriatics such as atrophine, homatropine, scopolamine, hydroxyamphetamine, ephedrine, cocaine, tropicamide, phenylephrine, cyclopentolate, oxyphenonium, eucatropine; and the like and mixtures thereof. Other useful therapeutic components include: antiglaucoma drugs, for example, timolol, and especially its maleic salt and R-timolol and a combination of timolol or R-timolol with pilocarpine; other adrenergic agonists and/or antagonists such as epinephrine and an epinephrine complex, or prodrugs such as bitartrate, borate, hydrochloride and dipivefrine derivatives; carbonic anhydrase inhibitors such as acetazolamide, dichlorphenamide, 2-(p-hydroxyphenyl)-thiothiophene-sulfonamide, 6-hydroxy-2-benzothiazole-sulfonamide, and 6-pivaloyloxy-2-benzothiazolesulfonamide; antiparasitic compounds and/or anti-protozoal compounds such as ivermectin, pyrimethamine, trisulfapidimidine, clindamycin and corticosteroid preparations; compounds having antiviral activity such as acyclovir, 5-iodo-2'-deoxyuridine (IDU), adenosine arabinoside (Ara-A), trifluorothymidine, interferon, and interferon-inducing agents such as poly I:C; antifungal agents such as amphotericin B, nystatin, flucytosine, natamycin and miconazole; anesthetic agents such as etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocalne; ophthalmic diagnostic agents, such as: (a) those used to examine the retina such as sodium fluorescein, (b) those used to examine the conjunctiva, cornea and lacrimal apparatus, such as fluorescein and rose bengal and (c) those used to examine abnormal pupillary responses such as methacholine, cocaine, adrenaline, atropine, hydroxyamphetamine and pilocarpine; ophthalmic agents used as adjuncts in surgery, such as alpha-chymotrypsin and hyaluronidase; chelating agents such as ethylenediaminetetraacetic acid (EDTA) and deferoxamine; immunosuppressants and anti-metabolites such as methotrexate, cyclophosphamide, 6-mercaptopurine and azathioprine and combinations of the compounds mentioned above, such as antibiotics/antiinflammatories combinations such as the combination of neomycin sulfate and dexamethasone sodium phosphate and combinations concomitantly used for treating glaucoma, for example, a combination of timolol maleate and aceclidine; and the like and mixtures thereof.

The therapeutic component may also include, without limitation, one or more of the following: steroids including fluorometholone, prednisolone, medrysone, dexamethasone and loteprednol; NSAIDS including, without limitation, ketorolac, flurbiprofen, diclofenac, ketoprofen and suprofen; Beta Blockers including, without limitation, timolol, betaxolol, carteolol, levobunolol and metiproanolol; miotics and sympathomimetics including without limitation, carbachol, piloarpine, dipivefrin and epinephrine; postaglandins including, without limitation, latanoprost, bimatoprost and travoprost; quinolones; antibacterials, including without limitation, ofloxacin, ciprofloxacin, norfloxacin, gatifloxacin, bacitracin, chloramphenicol, erythromycin, gentamicin, tobramycin, polymyxinB, neomycin, amikacin, vancomycin, ampicillin, kanamycin, penicillin, cefazolin and sulfacetamide; adrenergic anesthetics including without limitation, proparacaine and tetracaine; antifungals including, without limitation, amphotericin B, fluconazole, natamycin, miconazole, ketoconazole; mydriatics and cycloplegics such as phenylephrine, hydroxyamphetamine, atropine, cyclopentolate, homatropine, scopolamine and tropicamide; antihistamine, API cromolyn, levocabastin, naphazoline and antazoline and the like and mixtures thereof.

Certain steroids, such as testosterone and other insoluble drugs, such as cyclosporin may be solubilized utilizing surfactants or other solubilizers (e.g. cyclodextrin) as is familiar to those skilled in the art.

In one embodiment, the useful therapeutic components include adrenergic agonists. For example, the useful therapeutic components may include alpha-adrenergic agonists. Examples of alpha-adrengergic agonists include, but not limited to, adrafinil, adrenolone, amidephrine, apraclonidine, budralazine, clonidine, cyclopentamine, detomidine, dimetofrine, dipivefrin, ephedrine, epinephrine, fenoxazoline, guanabenz, guanfacine, hydroxyamphetamine, ibopamine, indanazoline, isometheptene, mephentermine, metaraminol, methoxamine, methylhexaneamine, metizolene, midodrine, naphazoline, norepinephrine, norfenefrine, octodrine, octopamine, oxymetazoline, phenylephrine, phenylpropanolamine, phenylpropylmethylamine, pholedrine, propylhexedrine, pseudoephedrine, rilmenidine, synephrine, tetrahydrozoline, tiamenidine, tramazoline, tuaminoheptane, tymazoline, tyramine, xylometazoline, and the like and mixtures thereof.

In one useful embodiment, the therapeutic components include alpha-2-adrenergic agonists. As used herein, the term "alpha-2 adrenergic agonist" includes chemical entities, such as compounds, ions, complexes and the like, that may produce a net sympatholytic response, resulting in increased accommodation, for example, by binding to presynaptic alpha-2 receptors on sympathetic postganglionic nerve endings or, for example, to postsynaptic alpha-2 receptors on smooth muscle cells. A sympatholytic response is characterized by the inhibition, diminishment, or prevention of the effects of impulses conveyed by the sympathetic nervous system. The alpha-2 adrenergic agonists of the invention may bind to the alpha-2 adrenergic receptors presynaptically, causing negative feedback to decrease the release of neuronal norepinephrine. Additionally, they also may work on alpha-2 adrenergic receptors postsynaptically, inhibiting beta-adrenergic receptor-stimulated formation of cyclic AMP, which contributes to the relaxation of the ciliary muscle, in addition to the effects of postsynaptic alpha-2 adrenergic receptors on other intracellular pathways. Activity at either pre- or postsynaptic alpha-2 adrenergic receptors may result in a decreased adrenergic influence. Decreased adrenergic influence results in increased contraction resulting from cholinergic innervations. Alpha-2 adrenergic agonists also include compounds that have neuroprotective activity. For example, 5-bromo-6-(2-imidozolin-2-ylamino) quinoxaline is an alpha-2-adrenergic agonist which has a neuroprotective activity through an unknown mechanism. Without limiting the invention to the specific groups and compounds listed, the following is a list of representative alpha-2 adrenergic agonists useful in this invention: imino-imidazolines, including clonidine, apraclonidine; imidazolines, including naphazoline, xymetazoline, tetrahydrozoline, and tramazoline; imidazoles, including detomidine, medetomidine, and dexmedetomidine; azepines, including B-HT 920 (6-allyl-2-amino-5,6,7,8 tetrahydro-4H-thiazolo[4,5-d]-azepine and B-HT 933; thiazines, including xylazine; oxazolines, including rilmenidine; guanidines, including guanabenz and guanfacine; catecholamines and the like and mixtures thereof.

Particularly useful therapeutic components, for example, alpha-2-adrenergic agonists, include quinoxaline components. In one embodiment, the quinoxaline components include quinoxalines, derivatives thereof, for example, and without limitation, ophthalmically acceptable acid additive salts thereof, and mixtures thereof.

Quinoxaline components particularly useful in accordance with the present invention include those having the following formula:

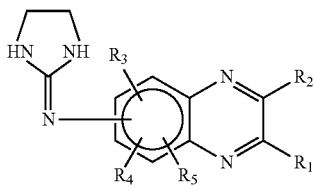

and ophthalmically acceptable acid addition salts thereof and mixtures thereof, wherein $R_1$ and $R_2$ each is independently selected from the group consisting of H, alkyl radicals containing 1 to 4 carbon atoms, for example, methyl radicals, and alkoxy radicals containing 1 to 4 carbon atoms, the 2-imidazolin-2-ylamino group may be in any of the 5-, 6-, 7-, or 8-positions of the quinoxaline nucleus, and the $R_3$, $R_4$ and $R_5$ each may be located in any one of the remaining 5-, 6-, 7-, or 8-positions of the quinoxaline nucleus and is independently selected from the group consisting of Cl, Br, H and alkyl radicals containing 1 to 3 carbon atoms, for example, a methyl radical. In one useful embodiment, both $R_1$ and $R_2$ of the quinoxaline component are H. In another useful embodiment, both $R_1$ and $R_2$ of the quinoxaline component are alkyl radicals which include 1 to 4 carbon atoms. In yet another useful embodiment, $R_3$ of the quinoxaline component is either H or a methyl radical. In still another useful embodiment, the 2-imidazolin-2-ylamino group is in the 6-position of the quinoxaline nucleus and $R_4$ and $R_5$ are both H. In yet another useful embodiment, the 2-imidazolin-2-ylamino group is in the 6-position of the quinoxaline nucleus, $R_3$ is either H or a methyl radical and $R_4$ and $R_5$ are both H.

For example, without limitation, the formula may be:

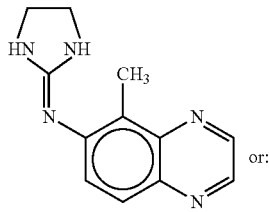

or:

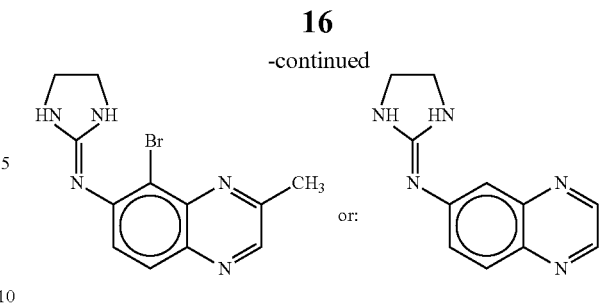

Non-limiting examples of quinoxaline derivatives include (2-imidozolin-2-ylamino) quinoxalines and 5-halide-6-(2-imidozolin-2-ylamino) quinoxalines, ophthalmically acceptable addition salts thereof and the like and mixtures thereof. The "halide" of the 5-halide-6-(2-imidozolin-2-ylamino) quinoxaline may be, for example, a fluorine, a chlorine, an iodine, or a bromine, to form, for example, 5-bromo-6-(2-imidozolin-2-ylamino) quinoxaline (brimonidine).

The alpha-2-adrenergic agonists, for example, the ones set forth herein, may be effective toward activating one or more of alpha-2A-adrenergic receptors, alpha-2B-adrenergic receptors and alpha-2D-adrenergic receptors.

Other quinoxalines and quinoxaline derivatives contemplated for use in the present invention are well known, for example, quinoxalines and quinoxaline derivatives disclosed by Danielwicz et al U.S. Pat. No. 3,890,319; Gluchowski U.S. Pat. No. 5,021,416; Burke et al U.S. Pat. No. 5,703,077; and Burke et al U.S. Pat. No. 5,773,440. The disclosure of each of Danielwicz et al U.S. Pat. No. 3,890,319; Gluchowski U.S. Pat. No. 5,021,416; Burke et al U.S. Pat. No. 5,703,077; and Burke et al U.S. Pat. No. 5,773,440 is incorporated in its entirety by reference herein.

Quinoxalines may be alpha-2 adrenergic agonists. Analogs of quinoxalines, for example and without limitation, the compounds set forth herein, that function as alpha-2 adrenergic agonists or other alpha-2 adrenergic agonists also are specifically contemplated for use in the present invention.

In one useful embodiment, the amount of quinoxaline component in the present composition is in the range of about 0.001% (w/v) to about 40% (w/v) of the composition, for example, in a range of about 0.01% (w/v) to about 10% (w/v). In one particularly useful embodiment, the quinoxaline component includes brimonidine, its ophthalmically acceptable acid addition salts and mixtures thereof and is present in an amount in a range of about 0.04% (w/v) to about 2% (w/v), for example, about 0.05% (w/v) to about 0.3% (w/v), such as about 0.15% (w/v).

The quinoxaline, for example, brimonidine, can be present as a charged molecule or as a free base. At pH 7.8, for example, a large fraction of the quinoxaline, for example, brimonidine, is present as a free base. A free base is more hydrophobic and therefore may more readily penetrate the cornea. Therefore, the free base form of the quinoxaline, for example, brimonidine, may be preferred.

Other useful therapeutic components include hypotensive lipid components such as disclosed in Woodward et al U.S. Pat. No. 5,688,819, combinations of lipid hypotensive components and timolol components as discussed in co-pending application Ser. No. 10/153,043 filed May 22, 2002; pyrano-quinolinone derivatives such as disclosed in Cairns et al U.S. Pat. No. 4,474,787, compounds having retinoid-like activities such as disclosed in Chandraratna U.S. Pat. No. 5,089,509, ketorolac/pyrrole-1-carboxylic acids such as disclosed in Muchowski et al U.S. Pat. No. 4,089,969, ofloxacins/benzox-azine derivatives such as disclosed in Hayakawa et al U.S. Pat. No. 4,382,892, memantines such as disclosed in Lipton et al U.S. Pat. No. 5,922,773 and the like and mixtures thereof. The disclosure of each of the above-noted Woodward et al patent, the co-pending application, and the Cairns et al, Chandraratna, Muchowski et al, Hayakawa et al and Lipton et al patents is incorporated in its entirety herein by reference.

In one embodiment, the hypotensive lipid component useful in the present compositions has the following formula (I)

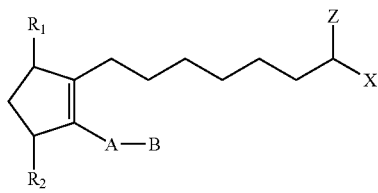

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of —$OR^4$ and —$N(R^4)_2$ wherein $R^4$ is selected from the group consisting of hydrogen, a lower alkyl radical having from one to six carbon atoms,

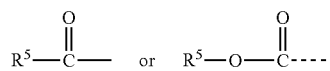

wherein $R^5$ is a lower alkyl radical having from one to six carbon atoms; Z is =O or represents 2 hydrogen radicals; one of $R_1$ and $R_2$ is =O, —OH or a —$O(CO)R_6$ group, and the other one is —OH or —$O(CO)R_6$, or $R_1$ is =O and $R_2$ is H, wherein $R_6$ is a saturated or unsaturated acyclic hydrocarbon group having from 1 to about 20 carbon atoms, or —$(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not —OR4. (That is, the cycloalkyl or hydrocarbyl aryl or heteroaryl radical is not substituted with a pendant radical having an atom other than carbon or hydrogen.)

In one embodiment, the hypotensive lipid component has the following formula II

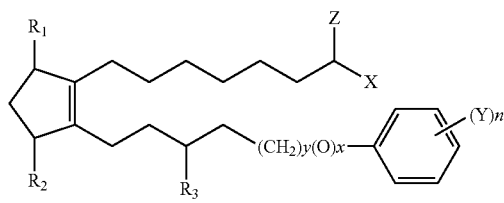

wherein y is 0 or 1, x is 0 or 1 and x and y are not both 1, Y is a radical selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. and n is 0 or an integer of from 1 to about 3 and $R_3$ is =O, —OH or —$O(CO)R_6$ wherein $R_6$ is as defined above. Preferably, n is 1 or 2.

Advantageously the hypotensive lipid component has the following formula (III).

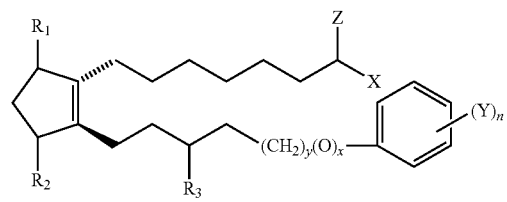

wherein hatched lines indicate a configuration, solid triangles are used to indicate configuration.

In one embodiment, the hypotensive lipid component has the following formula (IV)

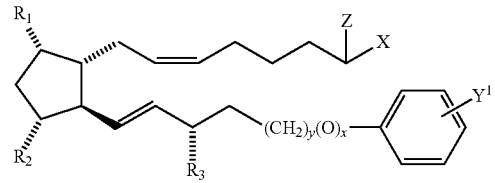

wherein $Y^1$ is Cl or trifluoromethyl and the other symbols and substituents are as defined above.

In a useful embodiment, the hypotensive lipid component has the following Formula (V)

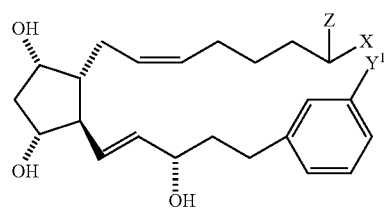

and the 9- and/or 11- and/or 15 esters thereof.

In one particularly useful embodiment, the hypotensive lipid component has the following structure Formula (VI)

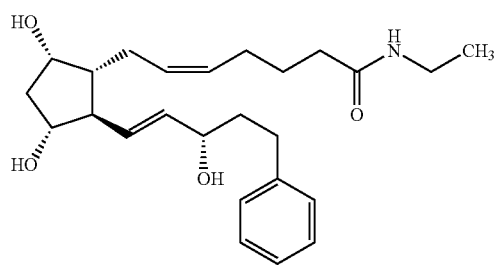 [SMILES: CCNC(=O)CCC/C=C\C[C@@H]1[C@@H](/C=C/[C@@H](O)CCc2ccccc2)[C@H](O)C[C@@H]1O]

known as bimatoprost. Bimatoprost is present at a concentration of 0.03% (w/v) in a composition sold by Allergan Inc. under the trademark Lumigan®.

The hypotensive lipid component preferably is present in the present compositions in an amount effective to reduce intraocular pressure when the composition is applied to a hypertensive eye. The preferred amount of hypotensive lipid component employed is in a range of about 0.00001% to about 1.0% (w/v), more preferably about 0.0001% to about 0.1% (w/v).

The following hypotensive lipid components may be used in the compositions of the present invention.
(1) cyclopentane heptenol-5-cis-2-(3 hydroxy-5-phenyl-1-trans-pentenyl)-3,5-dihydroxy,[1α,2β,3α,5α]
(2) cyclopentane heptenamide-5-cis-2-(3 hydroxy-5-phenyl-1-trans-pentenyl)-3,5-dihydroxy,[1α,2β,3α,5α]
(3) cyclopentane N,N-dimethylheptenamide-5-cis-2-(3 hydroxy-5-phenyl-1-trans-pentenyl)-3,5-dihydroxy,[1α,2β,3α,5α]
(4) cyclopentane heptenyl methoxide-5-cis-2-(3 hydroxy-5-phenyl-1-trans-pentenyl)-3,5-dihydroxy,[1α,2β,3α,5α]
(5) cyclopentane heptenyl ethoxide-5-cis-2-(3 hydroxy-4-meta-chlorophenoxy-1-trans-pentenyl)-3,5-dihydroxy,[1α,2β,3α,5α]
(6) cyclopentane heptenylamide-5-cis-2-(3 hydroxy-4-meta-chlorophenoxy-1-trans-pentenyl)-3,5-dihydroxy,[1α,2β,3α,5α]
(7) cyclopentane heptenylamide-5-cis-2-(3 hydroxy-4-trifluoromethylphenoxy-1-trans-pentenyl)-3,5-dihydroxy,[1α,2β,3α,5α]
(8) cyclopentane N-isopropyl heptenamide-5-cis-2-(3 hydroxy-5-phenyl-1-trans-pentenyl)-3,5-dihydroxy,[1α,2β,3α,5α]
(9) cyclopentane N-ethyl heptenamide-5-cis-2-(3 hydroxy-5-phenyl-1-trans-pentenyl)-3,5 dihydroxy,[1α,2β,3α,5α]
(10) cyclopentane N-methyl heptenamide-5-cis-2-(3 hydroxy-5-phenyl-1-trans-pentenyl)-3,5-dihydroxy,[1α,2β,3α,5α]
(11) cyclopentane heptenol-5-cis-2-(3 hydroxy-4-meta-chlorophenoxy-1-trans-butenyl)-3,5-dihydroxy,[1α,2β,3α,5α]
(12) cyclopentane heptenamide-5-cis-2-(3 hydroxy-4-meta-chlorophenoxy-1-trans-butenyl)-3,5-dihydroxy,[1α,2β,3α,5α]
(13) cyclopentane heptenol-5-cis-2-(3 hydroxy-5-phenyl-1-trans-pentenyl)3,5-dihydroxy,[1α,2β,3α,5α]

A pharmaceutically acceptable salt is any salt which retains the activity of the parent compound and does not impart any deleterious or undesirable effect on the subject to whom it is administered and in the context in which it is administered. With regard to the hypotensive lipid components, such salts are those formed with pharmaceutically acceptable cations, e.g., alkali metals, alkali earth metals, etc.

In one useful embodiment, the amount of therapeutic component in the present composition is in the range of about 0.001% (w/v) or less or about 0.005% (w/v) to about 30% (w/v) or about 40% (w/v) of the composition, for example, in a range of about 0.01% (w/v) to about 10% (w/v). In one particularly useful embodiment, the therapeutic component is present in an amount in a range of about 0.04% (w/v) to about 2% (w/v), for example, about 0.05% (w/v) to about 0.3% (w/v). In one embodiment, the amount of therapeutic component is in the range of about 0.01% (w/v) to about 1.0% (w/v).

The present compositions further include a carrier component, which preferably is ophthalmically acceptable.

A carrier component or other material is "ophthalmically acceptable" when it is compatible with ocular tissue. That is, it does not cause any significant or undue detrimental effects when brought into contact with ocular tissue. Preferably, the ophthalmically acceptable material is also compatible with other components of the present compositions.

The carrier component may include one or more components which are effective in providing such ophthalmic acceptability and/or otherwise benefiting the composition and/or the eye to which the composition is administered and/or the patient whose eye is being treated. Advantageously, the carrier component is aqueous-based, for example, comprising a major amount, that is at least about 50% by weight, of water.

Examples of suitable materials useful in the present carrier components include one or more of water, mixtures of water and water-miscible solvents such as lower alkanols or aralkanols, vegetable oils, polyalkylene glycols, petroleum-based jelly, ethyl cellulose, ethyl oleate, polyvinylpyrrolidone, isopropyl mirstate, other conventionally employed pharmaceutically acceptable materials and the like.

The carrier component may include an effective amount of a tonicity adjusting component to provide the composition with the desired tonicity. Among the suitable tonicity adjusting components that may be employed are those conventionally used in ophthalmic compositions, such as one or more various inorganic salts and the like. Sodium chloride, potassium chloride, mannitol, dextrose, glycerin, propylene glycol and the like and mixtures thereof are very useful tonicity adjusting components.

The carrier component preferably includes a buffer component which is present in an amount effective to maintain the pH of the composition in the desired range. Among the suitable buffer components or buffering agents that may be employed are those conventionally used in ophthalmic compositions. The buffer salts include alkali metal, alkaline earth metal and/or ammonium salts. Conventional organic buffers, such as Good's buffer and the like, may also be employed.

The carrier component may also include auxiliary substances such as emulsifiers, wetting agents, bodying agents, acids and/or bases, viscosity agents, lubricity components, preservative components, other materials useful in ophthalmic formulations and the like, including, but not limited to, such substances which are conventionally used in ophthalmic compositions.

The carrier component may be in various forms. In one embodiment, the carrier component comprises a liquid, and the composition may be a solution or a suspension. In either situation, the carrier may simply contain water and one or more auxiliary components noted elsewhere herein.

In one very useful embodiment the carrier component includes at least one of the following: an effective amount of a buffer component; an effective amount of a tonicity component; an effective amount of a preservative component; and water.

Examples of bodying agents optionally useful in the present invention include, but are not limited to, various polyethylene glycols, carbowaxes, and the like and mixtures thereof.

Acids optionally useful in the present compositions include boric acid, hydrochloric acid, acetic acid, other acids which are ophthalmically acceptable in the concentrations used, and the like and mixtures thereof.

Bases which may be included in the present compositions include, but are not limited to, sodium and/or potassium hydroxides, other alkali and/or alkaline earth metal hydroxides, organic bases, other bases which are ophthalmically acceptable in the concentrations used, and the like and mixtures thereof.

The acid/bases/buffers may be included, if at all, to provide and/or maintain the present compositions at a pH in the physiologically acceptable range, for example, in a range of about 4 to about 8.5, or in a range of about 6 to about 8, or in a range of about 6.8 to about 8.

Preservative components optionally useful in the compositions of the present invention include, but are not limited to, BAK (benzalkonium chloride), organo-mercurials, such as thiomerosal and phenylmercuric acetate and nitrate, quaternary ammonium compounds, methyl and propyl parabens, benzyl alcohol, phenylethanol and the like and mixtures thereof. Because of the antimicrobial activity of certain therapeutic components of the present compositions, the concentration of the preservative component, if present at all, in the present compositions may be reduced by at least about 10% or at least about 20%, relative to the concentration of the preservative needed in a similar composition without a therapeutic component.

The present compositions may include effective amounts of chelating or sequestering components, such as ethylene diamine tetraacetic acid (EDTA), citric acid, tartaric acid and the like.

Other optional excipients useful in the present compositions include stabilizing agents such as antioxidants, for example, alkali metal metabisulfates, ascorbic acid and the like.

These additional components preferably are ophthalmically acceptable and can be chosen from materials which are conventionally employed in ophthalmic compositions, for example, artificial tear formulations and the like.

Acceptable effective concentrations for these additional components in the compositions of the invention are readily apparent to the skilled practitioner.

In one embodiment, it is important that the preservative component be substantially unaffected by the presence of other components present in the compositions. The preservative component chosen depends on various factors, for example, the other components present in the composition. Examples of the useful preservative components include, but are not limited to, per-salts, such as perborates, percarbonates and the like; peroxides, such as very low concentrations, for example, about 50 to about 200 ppm (w/v), of hydrogen peroxide and the like; alcohols, such as benzyl alcohol, chlorbutanol and like; sorbic acid and ophthalmically acceptable salts thereof and mixtures thereof.

The amount of preservative component included in the present compositions containing such a component varies over a relatively wide range depending, for example, on the specific preservative component employed. The amount of such component may be in the range of about 0.000001% (w/v) to about 0.05% (w/v) or more of the present composition.

One particularly useful class of preservative components are chlorine dioxide precursors. Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide-containing complexes, such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas U.S. Pat. No. 3,278,447, which is incorporated in its entirety herein by reference. Specific examples of useful SCD products include those sold under the trademark Purite®, those sold under the trademark Dura Klor by Rio Linda Chemical Company, Inc., and those sold under the trademark Anthium Dioxide by International Dioxide, Inc.

A chlorine dioxide precursor may be included in the present compositions to effectively preserve the compositions. Such effective preserving concentrations can be in the range of about 0.0002% (w/v) or about 0.002% (w/v) to about 0.02% (w/v) of the present compositions.

In the event that chlorine dioxide precursors are employed as preservative components, the compositions can have an osmolality of at least about 200 mOsmol/kg and can be buffered to maintain the pH within an acceptable physiological range, for example, a range of about 6 to about 8 or about 10.

The present compositions can include an effective amount of an electrolyte component, that is one or more electrolytes, for example, such as is found in natural tears and artificial tear formulations. Examples of particularly useful electrolytes for inclusion in the present compositions include, without limitation, alkaline earth metal salts, such as alkaline earth metal inorganic salts, and mixtures thereof, for example, calcium salts, magnesium salts and mixtures thereof. Very good results are obtained using an electrolyte component selected from calcium chloride, magnesium chloride and mixtures thereof.

The amount or concentration of such electrolyte component in the present compositions can vary widely and depends on various factors, for example, the specific electrolyte component being employed, the specific composition in which the electrolyte is to be included and the like factors. In one useful embodiment, the amount of electrolyte component is chosen to at least partially resemble, or even substantially resemble, the electrolyte concentration in natural human tears. The concentration of the electrolyte component may be in the range of about 0.01% (w/v) to about 0.5% (w/v) or about 1% (w/v) of the present composition.

The present compositions can be prepared using conventional procedures and techniques. For example, the present compositions can be prepared by blending the components together, such as in one bulk.

To illustrate, in one embodiment, the components are combined with purified water and caused to disperse in the purified water, for example, by mixing and/or agitation. The final mixture is sterilized, such as steam sterilized, for example, at temperatures of at least about 100° C., such as in a range of about 120° C. to about 130° C., for a time of at least about 15 minutes or at least about 30 minutes, such as in a range of about 30 to about 60 minutes. In one embodiment, the preservative component is added to the mixture after sterilization. The final product may be filtered, for example, through a 20 micron sterilized cartridge filter, such as a 20 micron clarity filter cartridge, for example, sold by Pall under the trade name H.C. II, to provide a clear, smooth solution, which is then aseptically filled into containers, for example, low density polyethylene teal containers.

Alternately, the retention component can be mixed with purified water. The blended solution can then be combined with the other components, sterilized and filled into containers, as noted above.

In one particularly useful embodiment, a solution of the retention component and purified water is obtained, as noted above. This solution is then sterilized, for example, as noted above. Separately, the other components to be included in the final composition are solubilized in purified water. This latter solution is filter sterilized, for example, through a 0.2 micron filter, such as that sold by Pall under the trade name Suporflow. The filter sterilized solution is added to the retention component-containing solution to form the final solution. The final solution may be filtered, for example, as noted above, to provide a clear, smooth solution which is then aseptically filled into containers, as noted above.

The present compositions may be effectively used, as needed, by methods which comprise administering an effective amount of a composition to an eye, for example, an eye with an increased intraocular pressure relative to the intraocular pressure of a normal eye or to an eye having a propensity toward an increased intraocular pressure. The administering step may be repeated as needed to provide effective treatment to such eye. The mode of administration of the present composition depends on the form of the composition. For example, if the composition is a solution, drops of the composition may be applied to the eye, for example, from a conventional eye dropper. In general, the present compositions may be applied to the surface of the eye in substantially the same way as conventional ophthalmic compositions are applied. Such administration of the present compositions provides substantial and unexpected benefits, as described elsewhere herein.

The following non-limiting examples illustrate certain aspects of the present invention.

Example 1

An ophthalmic formulation in accordance with the present invention is prepared as follows:

A mixture of brimonidine purified water, high molecular weight sodium carboxymethylcelluloses (HCMC) and medium molecular weight sodium carboxymethylcelluloses (MCMC) is produced by blending the components together with mixing. The HCMC has a weight average molecular weight of about 700,000, while the MCMC has a weight average molecular weight of about 250,000. Both the HCMC and the MCMC are commercially available and are sold by Hercules under the trademark AQUALON®

Various other materials are blended with this mixture to form a solution having the following composition:

| Ingredient | Concentration, % (w/v) |
| --- | --- |
| Brimonidine Tartrate | 0.10 |
| HCMC | 0.30 |
| MCMC | 0.70 |
| Sodium Chloride | 0.37 |
| Boric Acid | 0.60 |
| Sodium Borate Decahydrate | 0.045 |
| Potassium Chloride | 0.14 |
| Calcium Chloride Dihydrate | 0.006 |
| Magnesium Chloride Hexahydrate | 0.006 |
| Sodium Hydroxide 1N | Adjust pH to 7.8 |
| Hydrochloric Acid 1N | Adjust pH to 7.8 |
| Purified water | q.s. ad |

The viscosity of this solution, measured by a conventional Brookfield viscometer, is 136 cps.

The solution is then heat sterilized in a closed autoclave, at 123° C. for 45 minutes.

A sterile Purite® solution is then added to the sterilized solution at a concentration of 0.0075% (w/v). Purite® is a registered trademark of Allergan, Inc. and the solution includes stabilized chlorine dioxide.

The viscosity of the sterilized solution measured by a conventional Brookfield viscometer, is 80 cps.

The sterilized solution, in the form of eye drops, is administered to the eyes of a patient having an elevated intraocular pressure compared to that of a normal eye. Such administration is effective to beneficially treat the patient's eyes. The beneficial treatment at least includes reducing the intraocular pressure of the eyes. Moreover, such treatment effectively provides a facilitated administration of brimonidine through the cornea of the patient's eyes requiring fewer administrations per unit time and/or a smaller application of the composition to the eye than would be required to produce the same beneficial effect utilizing a substantially identical composition which includes the same total amount of sodium carboxymethylcellulose without the HCMC.

In addition, the patient regains clear vision (that is non-blurry vision) more rapidly after administration of the composition relative to the time required to regain clear vision after administration of a substantially identical composition including the same total amount of sodium carboxymethylcellulose without the MCMC.

Examples 2 to 7

Example 1 is repeated an additional six (6) times except that the MCMC is replaced by low molecular weight sodium carboxymethylcellulose (LCMC), and various different ratios of HCMC and LCMC are used. The weight average molecular weight of the LCMC is 90,000. The LCMC is commercially available and is sold by Hercules under the trademark AQUALON®.

The amounts of HCMC and LCMC in each of these formulations and the viscosities of each of these formulations are as follows:

| | Example 2 | Example 3 | Example 4 | Example 5 | Example 6 | Example 7 |
| --- | --- | --- | --- | --- | --- | --- |
| HCMC, % w/v | 0.80 | 0.70 | 0.60 | 0.50 | 0.45 | 0.40 |
| LCMC, % w/v | 0.20 | 0.30 | 0.40 | 0.50 | 0.55 | 0.60 |

Viscosity

| | | | | | | |
| --- | --- | --- | --- | --- | --- | --- |
| After Sterilization | 248 cps | 132 cps | 94 cps | 59 cps | 63 cps | 38 cps |

Each of these sterilized solutions, in the form of eye drops, is administered to the eyes of a patient having glaucoma. Each such administration is effective to decrease the intraocular pressure of the patient's eyes. Moreover, advantageously such reduction lasts for a longer period of time per administration and/or less composition is required per administration to achieve a similar reduction relative to administering a substantially identical composition including the same total amount of sodium carboxymethylcellulose without the HCMC. In addition, each of the patients regains clear vision (that is non-blurry vision) more rapidly after administration of the sterilized solution relative to the time required to regain clear vision after administration of a substantially identical composition including the same total amount of sodium carboxymethylcellulose without the LCMC.

The sterilized solutions of Examples 2 to 7, when administered to the eyes of the patient, effectively provides for relief from glaucoma for relatively long periods of time.

Example 8

Figure 1B:
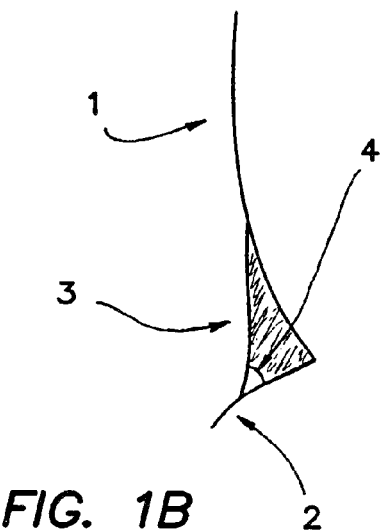
FIG. 1B shows the high contact angle of a composition of Example 1.

It is found that when a high surface tension composition is applied to an eye, it does not readily wet the periocular skin and therefore will not advance onto the facial surface by, for example, flowing over the lower eye lid. In cross-sectional images of the intersection of the cornea (1), lower lid (2) and tear meniscus (3), the advancing contact angle (4) of tear fluid mixed with two separate compositions can be seen (FIGS. 1A and 1B). FIG. 1A shows the contact angle of tear fluid mixed with a composition of Example 1 which includes HPMC in place of HCMC and MCMC. FIG. 1B shows the contact angle of tear fluid mixed with a composition of Example 1. The high advancing contact angle shown in FIG. 1B allows for a relatively high total volume of composition to remain in contact with the ocular surface.

Example 9

It is found that increased retention of a composition comprising a therapeutic component to the ocular surface can facilitate an enhanced, even substantially optimum, delivery of the therapeutic into the eye. Retention can be defined as or considered to be the proportion of composition added to an eye that remains on the eye over time.

Figure 2:
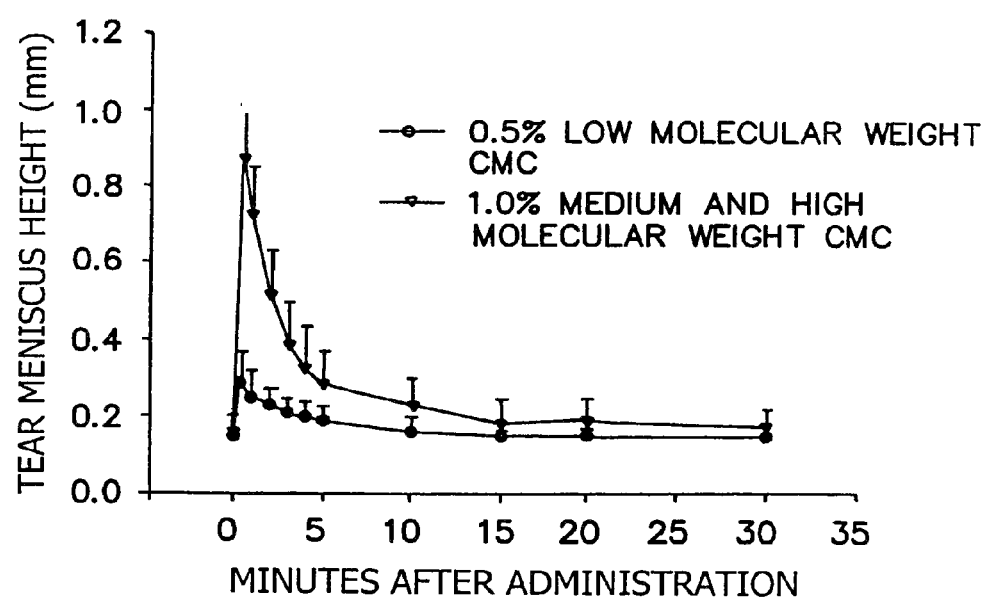
FIG. 2 shows a graph of a relationship of meniscus height to minutes of administration of a composition in accordance with the present invention.

FIG. 2 shows the meniscus height on the eyes over time of a composition comprising 1% (w/v) medium molecular weight and high molecular weight carboxymethylcellulose and a composition comprising 0.5% (w/v) low molecular weight carboxymethylcellulose. The average molecular weight of the medium molecular weight carboxymethylcellulose is about 250,000. The average molecular weight of the high molecular weight carboxymethylcellulose is about 700,000. The average molecular weight of the low molecular weight carboxymethylcellulose is about 90,000.

It can be seen that a greater meniscus height for the composition comprising the high molecular weight carboxymethylcellulose is retained on the eye relative to the meniscus height of the 0.5% (w/v) low molecular weight carboxymethylcellulose. This greater meniscus height of the composition including high molecular weight carboxymethylcellulose provides for a greater volume of composition being retained on the eye over time relative to the meniscus height of the composition including 0.5% (w/v) low molecular weight carboxymethylcellulose.

Example 10

Example 1 is repeated except that a hypotensive lipid component, that is such a component identified as bimatoprost, in a concentration of 0.02% (w/v) is used in place of the brimonidine tartrate.

The sterilized solution, in the form of eye drops, is administered to the eyes of a patient having an elevated intraocular pressure compared to that of a normal eye. Such administration is effective to beneficially treat the patient's eyes. The beneficial treatment at least includes reducing the intraocular pressure of the eyes. Moreover, such treatment effectively provides a facilitated administration of bimatoprost through the cornea of the patient's eyes requiring fewer administrations per unit time and/or a smaller application of the composition to the eye than would be required to produce the same beneficial effect utilizing a substantially identical composition which includes the same total amount of sodium carboxymethylcellulose without the HCMC.

In addition, the patient regains clear vision (that is non-blurry vision) more rapidly after administration of the composition relative to the time required to regain clear vision after administration of a substantially identical composition including the same total amount of sodium carboxymethylcellulose without the MCMC.

While this invention has been described with respect to various specific examples and embodiments, it is to be understood that the invention is not limited thereto and that it can be variously practiced within the scope of the following claims.

What is claimed is:

1. A topical ophthalmic solution consisting of:
    water;
    ketorolac, or a pharmaceutically acceptable salt thereof, in a range of 0.01% to 1.0% w/v;
    a mixture of medium molecular weight carboxymethyl cellulose and high molecular weight carboxymethyl cellulose wherein the medium and high molecular weight carboxymethyl cellulose is present in the solution in an amount of 0.1% w/v to 2.0% w/v and have a weight ratio between 0.25 and 4;
    sodium hydroxide and hydrochloric acid to adjust the pH;
    sodium chloride;
    a buffer; and
    having a pH in a range of about 6 to about 8.

2. The composition of claim 1, wherein the each of the medium and high molecular weight carboxymethyl cellulose is sodium carboxymethyl cellulose.

3. A topical ophthalmic solution consisting of:
    water;
    ketorolac, or a pharmaceutically acceptable salt thereof, in a range of 0.01% to 1.0% w/v;
    a mixture of medium molecular weight carboxymethyl cellulose and high molecular weight carboxymethyl cellulose wherein the medium and high molecular weight carboxymethyl cellulose is present in the solution in an amount of 0.1% w/v to 2.0% w/v and have a weight ratio between 0.25 and 4;
    sodium hydroxide and hydrochloric acid to adjust the pH;
    sodium chloride;
    a preservative;
    a buffer; and
    having a pH in a range of about 6 to about 8.

4. The topical ophthalmic solution of claim 1, wherein ketorolac is ketorolac tromethamine.

5. The topical ophthalmic solution of claim 1, wherein the sodium hydroxide and hydrochloric acid are 1N.

6. The topical ophthalmic solution of claim 1, wherein the solution has a pH of about 6.8.

7. The topical ophthalmic solution of claim 3, wherein the preservative is selected from the group consisting of benzalkonium chloride and chlorine dioxide.

8. The topical ophthalmic solution of claim 3, wherein ketorolac is ketorolac tromethamine.

9. The topical ophthalmic solution of claim 3, wherein sodium hydroxide and hydrochloric acid are 1N.

10. The topical ophthalmic solution of claim 3, wherein the solution has a pH of about 6.8.

* * * * *